(12) United States Patent
Banerjee et al.

(10) Patent No.: US 9,563,266 B2
(45) Date of Patent: Feb. 7, 2017

(54) HAPTIC AUGMENTED AND VIRTUAL REALITY SYSTEM FOR SIMULATION OF SURGICAL PROCEDURES

(71) Applicant: IMMERSIVE TOUCH, INC., Westmont, IL (US)

(72) Inventors: P. Pat Banerjee, Westmont, IL (US); Cristian J. Luciano, Evergreen Park, IL (US)

(73) Assignees: IMMERSIVETOUCH, INC., Westmont, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 543 days.

(21) Appl. No.: 13/628,841

(22) Filed: Sep. 27, 2012

(65) Prior Publication Data

US 2014/0088941 A1    Mar. 27, 2014

(51) Int. Cl.
*G06F 3/01*         (2006.01)

(52) U.S. Cl.
CPC ............... *G06F 3/011* (2013.01); *A61B 34/30* (2016.02); *A61B 34/76* (2016.02); *G06F 3/016* (2013.01)

(58) Field of Classification Search
None
See application file for complete search history.

(56) References Cited

U.S. PATENT DOCUMENTS

| | | | |
|---|---|---|---|
| 5,522,823 A | 6/1996 | Kuntz | |
| 5,769,640 A * | 6/1998 | Jacobus | B25J 9/1689 434/262 |
| 6,109,270 A | 8/2000 | Mah et al. | |
| 6,506,199 B2 | 1/2003 | Rogers et al. | |
| 6,567,687 B2 | 5/2003 | Front et al. | |
| 6,709,043 B2 | 3/2004 | Beusse et al. | |
| 7,812,815 B2 | 10/2010 | Banerjee et al. | |
| 8,133,172 B2 | 3/2012 | Shachar et al. | |
| 8,167,808 B2 | 5/2012 | Sato | |
| 2007/0035511 A1 | 2/2007 | Banerjee et al. | |
| 2007/0118135 A1 | 5/2007 | Mansmann | |
| 2008/0297535 A1* | 12/2008 | Reinig | G02B 27/2235 345/633 |
| 2009/0253109 A1* | 10/2009 | Anvari et al. | 434/262 |
| 2009/0306491 A1 | 12/2009 | Haggers | |
| 2011/0112434 A1 | 5/2011 | Ghabrial et al. | |
| 2011/0238079 A1 | 9/2011 | Hannaford et al. | |
| 2013/0230837 A1* | 9/2013 | Meglan et al. | 434/262 |

OTHER PUBLICATIONS

Erel et al. Microsurgery, 23:147-152, 2003.*
Mattos et al. Intelligent Robots and Systems (IROS), 2011 IEEE/RSJ International Conference on, san-Francisco, CA, 2011, p. 1359-1365.*
Wang et al. Engineering in Medicine and Biology Society, 2008, p. 1935-1938.*
Brown et al. Medical Image Computing and Computer-Assisted Intervention—MICCAI 2001 Lecture Notes in Computer Science. vol. 2208, 2001, pp. 137-144.*
International Search Report and Written Opinion from PCT/US2013/060629 issued on Apr. 10, 2014.
International Preliminary Report on Patentability from PCT/US2013/060629 mailed Jun. 18, 2015.
Official Communication from European Patent Application No. 13840563.4 dated Jul. 28, 2016.
Bornik et al. "Computer Aided Liver Surgery Planning: An Augmented Reality Approach" Optomechatronic Micro/Nano Devices and Components III: Oct. 8-10, 2007, Lausanne, Switzerland; Proceedings of SPIE, ISSN 0277-786X], SPIE, Bellingham, Wash, vol. 5029, Feb. 15, 2003 (Feb. 15, 2003), pp. 395-406.

* cited by examiner

*Primary Examiner* — Michael Borin
(74) *Attorney, Agent, or Firm* — Jennifer Lacroix; DLA Piper LLP (US)

(57) ABSTRACT

The present technology relates to systems, methods and devices for haptically-enabled virtual reality simulation of cerebral aneurysm clipping, wherein a user uses two physical stations during the simulation. The first station is a haptic and augmented reality station, and the second station is a haptic and virtual reality station.

9 Claims, 12 Drawing Sheets

HAPTIC AUGMENTED AND VIRTUAL REALITY SYSTEM FOR SIMULATION OF SURGICAL PROCEDURES

FIELD OF THE INVENTION

The present technology relates to methods, devices and systems for haptically-enabled simulation of cerebral aneurysm clipping using a haptic augmented and virtual reality system that includes an open surgery station that simulates performance of open surgery steps and a microsurgery station for simulates performance of microsurgery steps.

DESCRIPTION OF RELATED ART

Brain aneurysms are associated with a very significant mortality and morbidity related to stroke in previously healthy young patients, as well as older patients. Aneurysm clipping is an important procedure for large and complex aneurysms which cannot be treated by aneurysm coiling methods. Additionally, regardless of the complexity of the aneurysm itself, it regularly takes medical residents up to six months just to learn how to approach the aneurysm location surgically by pterional craniotomy and Sylvian fissure dissection. Moreover, in studying surgical methods of aneurysm clipping, there are also many elements of surgical judgment to be learned, such as optimal operative angle from which to approach the aneurysm, which affects craniotomy placement.

BRIEF DESCRIPTION OF THE DRAWINGS

Specific examples have been chosen for purposes of illustration and description, and are shown in the accompanying drawings, forming a part of the specification.

FIG. 168 illustrates one example of a virtual spherical drill bit that can be provided in an instrument library in a haptic augmented and virtual reality system of the present technology.

DETAILED DESCRIPTION

The present technology includes haptic augmented and virtual reality methods, systems and devices for performing simulated surgical procedures that include open surgery steps and microsurgery steps, including but not limited to cerebral aneurysm clipping.

Simulation methods of the present technology for cerebral aneurysm clipping can include all aspects of an aneurysm surgical procedure, including, for example, craniotomy, dural opening, dissection of the Sylvian fissure, clipping of an MCA (middle cerebral artery) bifurcation aneurysm, and flow testing of the patency of the parent vessel. The methods, devices, and systems of the present technology can be used with comprehensive surgery simulation systems that use both an open surgery station and a microsurgery station so as to simulate both open views of virtual patient anatomy and microscopic views of virtual patient anatomy.

As used herein, the term "open surgery station" should be understood to mean that an environment is provided in which the visual display provided to a user includes virtual reality aspects superimposed over real reality, and in which a user can see aspects of real reality in addition to the superimposed virtual reality aspects while performing steps of simulated open surgery. For example, at an open surgery station, a user can interact with displayed virtual patient anatomy, and a simulated surgical instrument can be displayed in a manner that it appears to be held in the actual hand of a user holding a haptic stylus as a proxy for the instrument.

As used herein, the term "microsurgery station" should be understood to mean that an environment is provided in which the visual display provided to a user consists of virtual aspects, which are computer generated graphics, that the user can see while performing steps of simulated microsurgery. For example, at a microsurgery station, a user can interact with displayed virtual patient anatomy using displayed virtual surgical instruments, and although the user uses a haptic stylus as a proxy for the instrument, the user does not see aspects of real reality.

Haptic Augmented and Virtual Reality Systems

Figure 1:
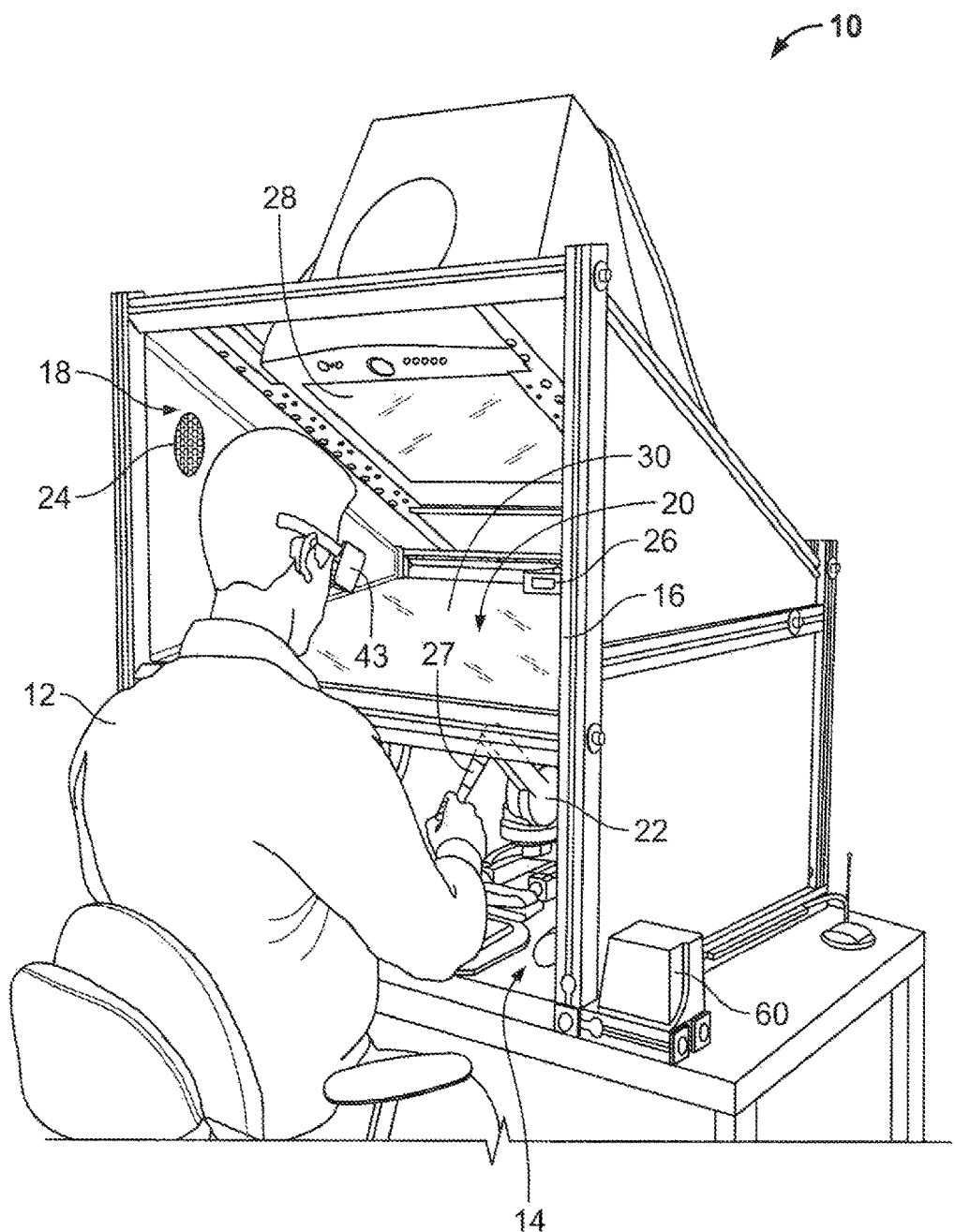
FIG. 1 illustrates a perspective schematic view of one example of a known open surgery station, which can be used in a haptic augmented and virtual reality system of the present technology.
Figure 2:
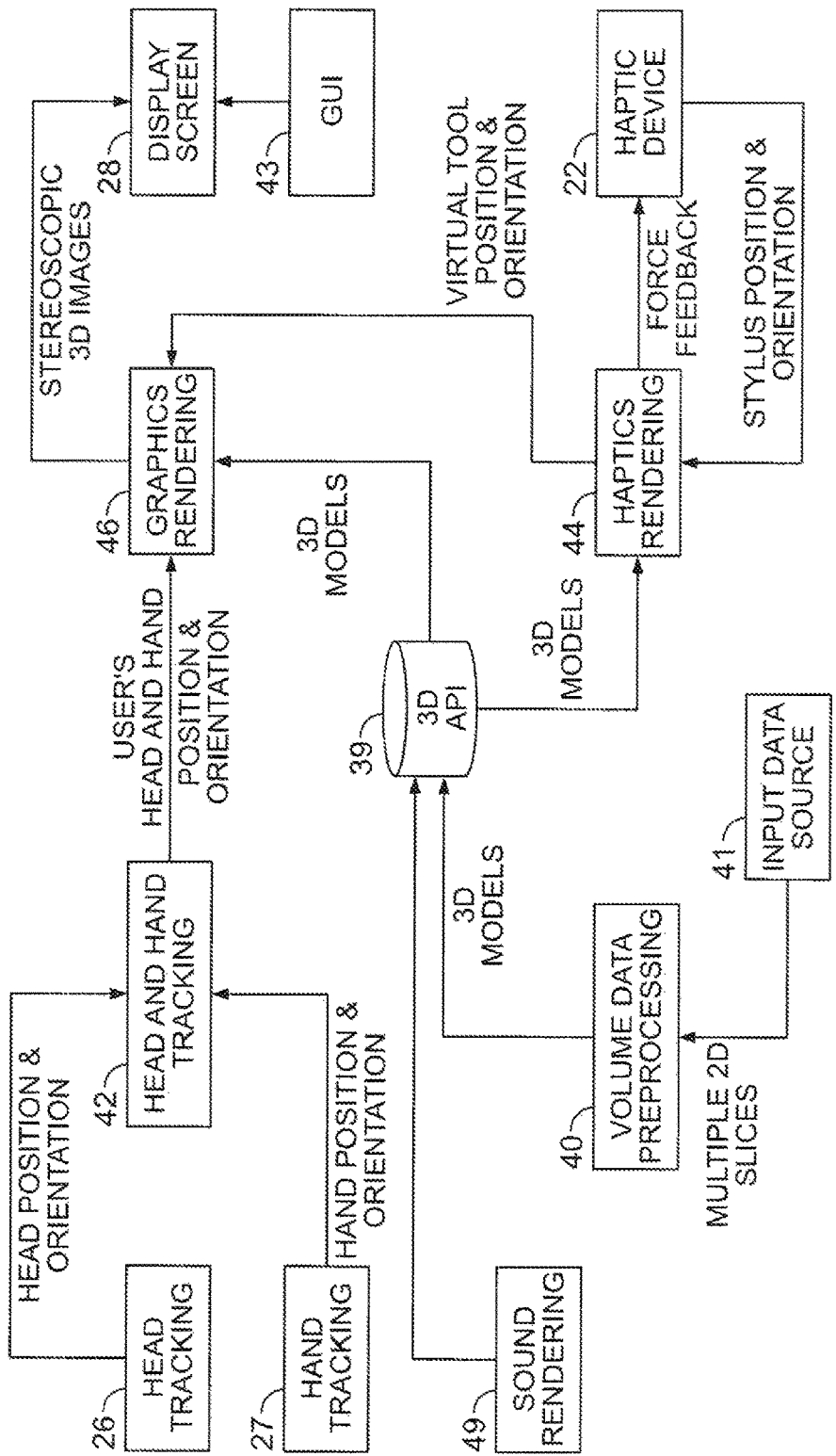
FIG. 2 illustrates a block diagram of a known software and hardware architecture for the system of FIG. 1.
Figure 3:
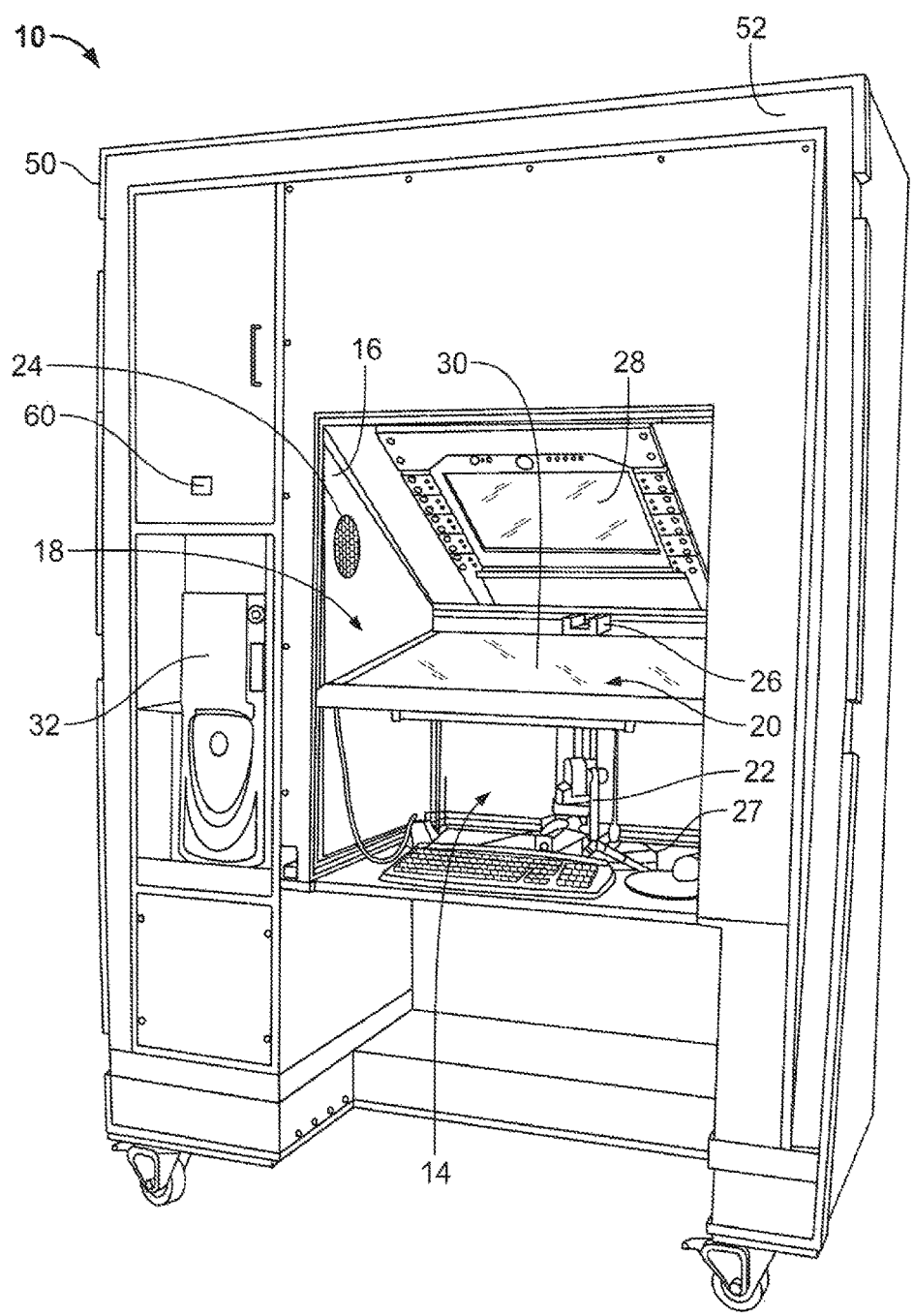
FIG. 3 illustrates a second perspective schematic view of the open surgery station of FIG. 1.
Figure 4:
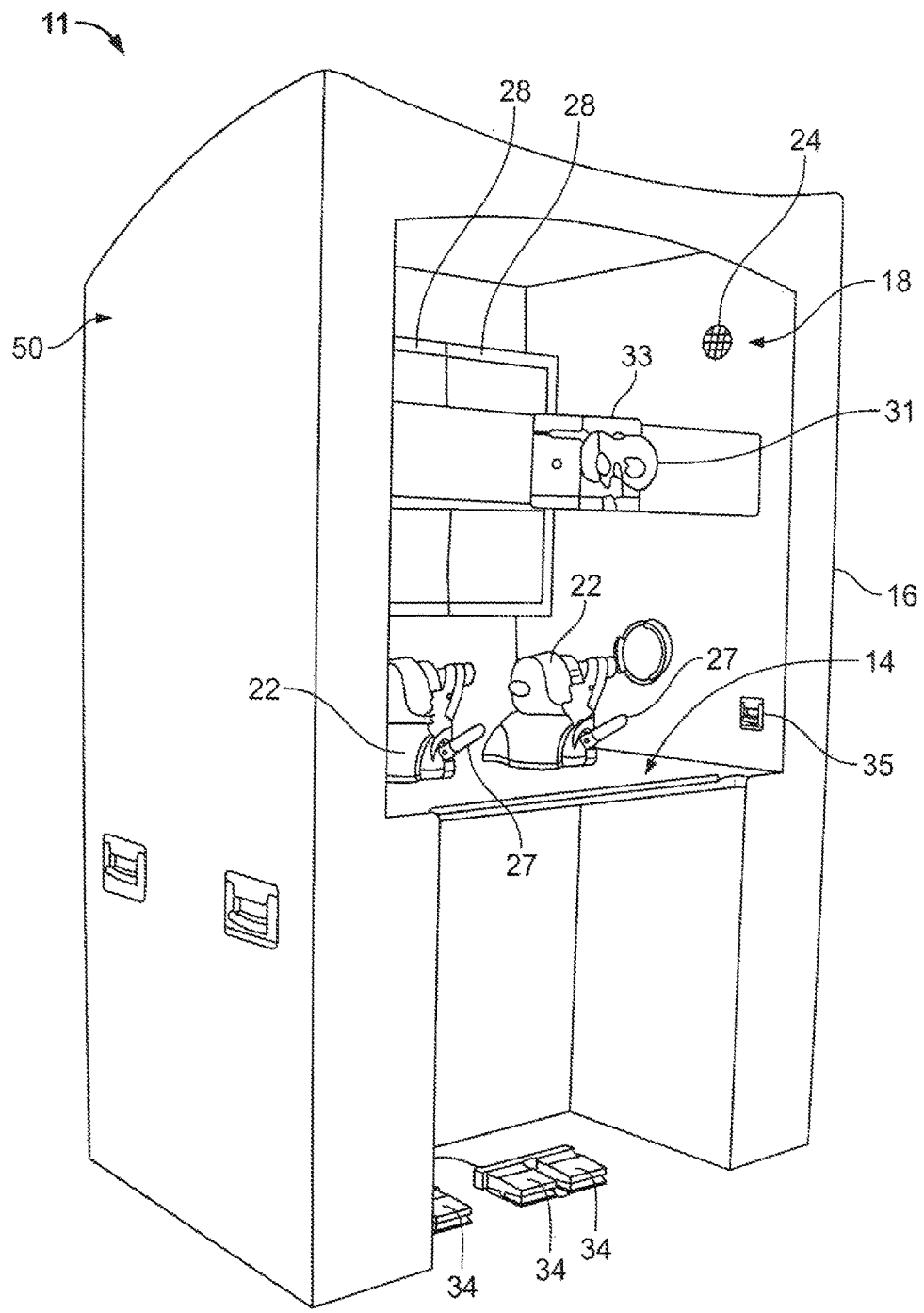
FIG. 4 illustrates a perspective schematic view of one example of a microsurgery station of the present technology, which can be used in a haptic augmented and virtual reality system of the present technology.

As discussed above, haptic augmented and virtual reality systems of the present technology can include an open surgery station 10 that simulates open surgery, one example of which is illustrated in FIGS. 1 and 3, and a microsurgery station 11 that simulates microsurgery, one example of which is illustrated in FIG. 4. Stations 10 and 11 can both include some of the same types of physical components, and for ease of reference like physical components are labeled with like reference numbers for both stations 10 and 11 in FIGS. 1-5.

Some examples of open surgery stations that can be used in the present technology are described in U.S. Pat. No. 7,812,815, which is hereby incorporated by reference in its entirety. With reference to the open surgery station 10 for simulating open surgical steps, the user 12 can sit or stand at a physical desktop workspace 14 defined by a housing 16 that has an opening 18 on one side. The open surgery station 10 can include a multi-sensorial computer interface that includes a stereoscopic vision interface 20, at least one haptic device 22, and a 3D sound system 24. Additionally, a head tracking device 26 and a hand tracking device in the form of at least one haptic robot stylus 27 can provide information regarding the user's interaction with the system as well as the user's visual perspective relating to the open surgery station 10.

With reference to the microsurgery station 11 for simulating microsurgical steps, the user (not shown in FIG. 4) can sit or stand at a physical desktop workspace 14 defined by a housing 16 that has an opening 18 on one side. The microsurgery station 11 can include a multi-sensorial computer interface that includes a binocular surgical microscopic eyepiece 31, at least one haptic device 22, and a 3D sound system 24. Additionally, a hand tracking device in the form of at least one haptic robot stylus 27 can provide information regarding the user's interaction with the system as well as the user's visual perspective relating to the microsurgery station 11.

Surgical procedures that can be simulated using haptic augmented and virtual reality systems of the present technology can include procedures that use a one-handed technique, or that require use of multiple hands. Accordingly, the open surgery station 10 and the microsurgery station 11 can each include at least one, or two, haptic devices 22, which track the user's hand position and orientation and provide force feedback to the user. For example, since many parts of aneurysm clipping procedures tend to require a two-handed technique, the methods of aneurysm clipping simulation provided herein can include the simultaneous use of two haptic devices 22. A 3D image of a first surgical tool can be collocated with a first haptic device 22, and an image of a second surgical tool can be collocated with a second haptic device 22. For example, the simulation method can include a user holding a first haptic device 22 in a first hand, such as the right hand, and superimposing an image of a first surgical tool, such as an aneurysm clip holder or an arachnoid knife over the first haptic device 22. The simulation method can also include a user holding a second haptic device 22 in a second hand, such as the left hand, and superimposing an image of a second surgical tool, such as a suction tip over the second haptic device 22. Other surgical tools can also be simulated, such as a bipolar electrocautery tip, microscissors, and other instruments, as appropriate.

The open surgery station 10 and the microsurgery station 11 can each include a display system that allows the user to acquire depth perception. Each display system can be driven by graphics logic, which can control and update the graphics displayed by the display system. The display system of the open surgery station 10 can use a display screen 28 that can be a single passive stereo monitor, a half-silvered mirror 30 to reflect the image of the display screen 28, and a head tracking system 26 to display a dynamic viewer-centered perspective. The partially transparent mirror 30 can permit the user 12 to see both the virtual reality display and the user's hands, thus providing an augmented reality environment. The user can hold and manipulate the haptic device 22 with its stylus 27 below the mirror 30. The display system of the microsurgery station 11 can display a static perspective by using two display screens 28, which can be non-stereo monitors located side by side and a binocular surgical eyepiece 31, which can consist of four first-surface mirrors oriented at an angle in such a way that the image of the left monitor is only seen by the left eye, and the image of the right monitor is only seen by the right eye. The orientation and distance between the front-surface mirrors can be adjusted by the user to match his/her interocular distance.

In the open surgery station 10, a virtual projection plane can be located exactly at the center of the haptic workspace and oriented perpendicular to that line, whereas in the microsurgery station 11 the user can view the virtual projection through the binocular surgical microscopic eyepiece 31. In the open surgery station 10 the partially transparent mirror 30 can preferably be sufficiently wide to allow the user to view virtual objects from different viewpoints (displaying the correct viewer-centered perspective) while permitting a comfortable range of movement. In contrast, in the microsurgery station 11, the binocular surgical microscopic eyepiece 31 can be adjusted up or down, either manually or by an automatic up-down adjustor, and the interocular distance can also be adjusted for comfortable 3-dimensional viewing. In one example, the height of the binocular surgical microscopic eyepiece 31 can be adjusted by adjusting the eyepiece mounting frame 33 can be adjusted up or down by activating a first foot pedal 34 or by a hand switch 35 on housing 16. In some examples, one or more additional foot pedals 34 can be provided to activate certain simulated surgical instruments such as a bipolar electrocautery forceps 68 as discussed below with reference to FIG. 5.

The computer 32 illustrated in FIG. 3 can be operatively connected to both the open surgery station 10 and the microsurgery station 11. Alternatively, the open surgery station 10 and the microsurgery station 11 can each be operatively connected to a separate computer 32, and in one example the separate computers can be linked via a wireless or wired network connection. The one or more computers can be components of a haptic augmented and virtual reality system that includes open surgery station logic that controls and operates the open surgery station 10, and microsurgery station logic that controls and operates the micro-surgery station 1. The haptic augmented and virtual reality system can include a software library that provides, in real time, a high level layer that encapsulates the rendering of a scene graph on either display screen 28, the stereoscopic vision interface 20, the handling of the hand tracking device shown as a haptic robot stylus 27, an interface with a haptic device 22, and playback of 3D spatial audio on a 3D sound system 24.

With respect to the open surgery station 10, a computer 32 can include haptics rendering logic that drives each haptic device of the open surgery station 10, and graphics logic that drives the display system of the open surgery station 10. The computer 32 connected to the open surgery station 10 can also include open surgery station logic, which can integrate the haptics rendering logic and the graphics logic and provide real-time simulation of open surgery steps of a surgical procedure, including updating the open surgical views in real time in response to user operations performed with a haptic device of the open surgery station 10. The open surgery station logic can also include an instrument library that includes a plurality of virtual surgical instruments that can each be selected by a user and displayed by the display system of the open surgery station 10. Some examples of instruments that can be included in the instrument library for use with the open surgery station 10 are discussed below with respect to the open surgery steps of the aneurysm clipping methodology.

With respect to the micro-surgery station 11, a computer 32 can include haptics rendering logic that drives each haptic device of the micro-surgery station 11, and graphics logic that drives the display system of the micro-surgery station 11. The computer 32 connected to the micro-surgery station 11 can also include microsurgery station logic, which can integrate the haptics rendering logic and the graphics logic and provide real-time simulation of open surgery steps of a surgical procedure including updating the microsurgical surgical views in real time in response to user operations performed with a haptic device of the micro-surgery station 11. The micro-surgery station logic can also include an instrument library that includes a plurality of virtual surgical instruments that can each be selected by a user and displayed by the display system of the micro-surgery station 1. Some examples of instruments that can be included in the instrument library for use with the micro-surgery station 11 are discussed below with respect to the micro-surgery steps of the aneurysm clipping methodology.

Referring now to FIG. 2, one example of a software and hardware architecture for a open surgery station 10 is shown. The architecture includes interconnected devices and software modules, which are integrated by a 3D application program interface (API) 39.

Figure 5:
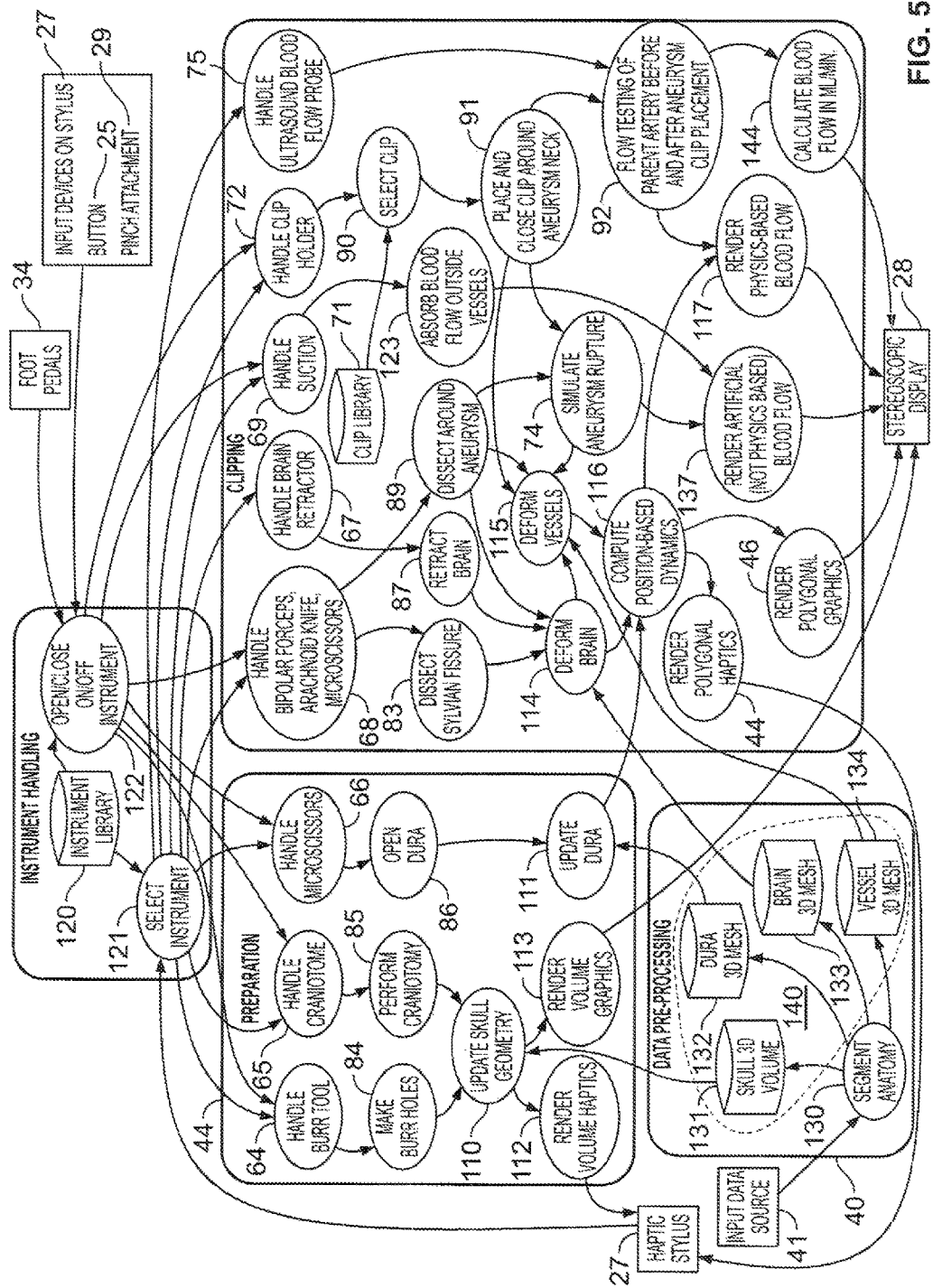
FIG. 5 illustrates a block diagram of one example of a method of performing simulated cerebral aneurysm clipping with a haptic augmented and virtual reality system of the present technology.

FIG. 2 for the open surgery station 10 and FIG. 5 for both the open surgery station 10 and the microsurgery station 11 include software and hardware for generating image data from scans of actual human anatomy. The volume data pre-processing 40 can receive 2D image data, for example, generated by an input data source 41, which can be a medical scanner. The volume data pre-processing 40 can provide 3D models to the 3D application program interface 39.

Examples of medical scanners that can be used as an input data source 40 for characterizing physical objects include a magnetic resonance imaging (MRI) scanner or a CT scanner, such as those typically used for obtaining medical images. The volume data pre-processing 40 segments and combines the 2D images to create a virtual 3D volume of the sample that was scanned, for example a human head. In an example embodiment for medical images that could be used, for example, for surgical training, the volume data pre-processing 40 creates detailed 3D structures. The characteristics of the various 3D structures will, with the interface to a haptic device 22, present different feel characteristics in the virtual reality environment, e.g. skin will feel soft and bone hard. Haptics rendering software 44 can monitor and control each haptic device 22 including each stylus 27. The haptics rendering software 44 can read the position and orientation of each haptic device 22, for example a stylus 27, or a plurality of styluses 27 for different functions or for use by separate hands, and computes collision detections between a virtual device corresponding to the haptic device 22 and objects within the 3D virtual environment. The haptics rendering software 44 can also receive 3D models from the 3D application program interface 39. For example, collisions with a virtual device and imported 3D isosurfaces can be computed, and the haptics rendering software can direct a haptic device 22 to generate the corresponding force feedback. In some examples, each isosurface is assigned different haptic materials, according to certain parameters: stiffness, viscosity, static friction and dynamic friction, as well as different physical properties such as density, mass, thickness, damping, bending, etc. Therefore, the user 12 can feel the different surfaces and textures of objects and surfaces in the virtual environment.

In a surgical simulation example, the user 12 can feel different sensations when touching skin, bone, and internal organs, such as the brain. In a preferred embodiment, the graphics and haptics can be on two separate threads, which can be implemented, for example with a dual processor computer. The haptics and graphics have their own update schedule, for example, haptics at 1000 Hz and graphics at about 30 Hz. In that example, the system would synchronize the two consecutive graphics update after about every 30 haptic updates, and it is within the skill of artisans to modify the manner in which haptics and graphics update and synchronize.

Hand tracking is very useful because it allows users to use both hands to interact with the virtual scene. While the user can feel tactile sensations with a hand holding a haptic stylus 27, it is also possible to use a tracked hand to move the 3D objects, manipulate lights, or define planes in the same 3D working volume. Graphics rendering software 46 receives 3D models from the 3D application program interface 39. Also, the graphics rendering software 46 receives virtual tool(s) information from the haptics rendering software 44. With the models and other information, the graphics rendering software 46 software generates and continuously updates, in real time, the stereoscopic 3D display that is displayed by a display screen 28.

The API 39 can provide a camera node that computes the correct viewer-centered perspective projection on the virtual projection plane. It can properly render both left and right views according to the position and orientation of the user's head given by the tracking system.

Sound rendering 49 can also used to add auditory simulations to a virtual environment through each 3D sound system 24. One example of sound rendering software is Open Audio Library (OpenAL), which is a freely-available cross-platform 3D audio API that serves as a software interface to audio hardware. OpenAL is can generate arrangements of sound sources around a listener in a virtual 3D environment. It handles sound-source directivity and distance-related attenuation and Doppler effects, as well as special effects such as reflection, obstruction, transmission, and reverberation.

Simulation of Aneurysm Clipping

Methods of the present technology include virtual reality simulation of aneurysm clipping surgical procedures, and can include simulation of one or more portions of such procedures, or even the entire procedure. The methods can include, for example, simulation of procedures including craniotomy, dural opening, navigation along the Sylvian fissure, clipping of the aneurysm, and flow testing of the patency of the parent vessel. In some examples, the Sylvian fissure can be presented as being pre-dissected, but can have elastic tissue boundaries. Additionally, flow testing of the patency of the parent vessel can be provided by suitable virtual instruments, such as a quantitative microvascular ultrasonic flowmeter (e.g., Charbel Micro-Flowprobe® of Transonic Systems), or a virtual gamma camera that visualizes a virtual injection of an indocyanine green (ICG) cyanine dye used for diagnostic fluorescence angiography. A virtual gamma camera can be simulated, for example, by a grayscale rendering of the blood vessels based on flow intensity.

One example of an aneurysm clipping method that can be performed using a haptic augmented and virtual reality system of the present technology is shown in FIG. 5. In the illustrated example, the open surgery steps of aneurysm clipping can be performed by a user located at a open surgery station 10, and can include burr hole drilling 84, craniotomy 85, and dural opening 86. The microsurgical steps, can be performed by a user located at a microsurgery station 11, and can include Sylvian fissure dissection 83, aneurysm clip selection task 90 from clip library 71 and held in clip holder 72, tissue dissection task 89 around the aneurysm and its parent vessel, aneurysm clip placement and closure on aneurysm neck 91, blood flow testing 92 with ultrasound flow sensor 75, and optional aneurysm rupture and repair 74.

As discussed above, the haptic augmented and virtual reality system can perform data pre-processing 40 by first receiving patient-specific medical imaging input data from an input data source 41. The data may be provided and received in a standard format such as DICOM. The DICOM or other input data received by the can be originally in the form of two-dimensional (2D) slices of patient anatomy. During data pre-processing 40, the segment anatomy pre-processing module can convert the 2D data into 3D format.

For the case of simulated cerebral aneurysm clipping, the 3D outputs of the segment anatomy module 130 can include the virtual patient's skull 3D volume 131, the dura mater 3D mesh 132, the brain 3D mesh 133, and the blood vessel 3D mesh 134, including the aneurysm neck and sac and parent artery. These four 3D anatomical outputs for the brain, enclosed within a dotted line and numbered together as item 140 in FIG. 5, constitute a suite of pre-processed virtual brain elements and may be referred to as a virtual patient case. The numeral 140 symbolizes both an individual patient case and any other such cases that can be stored permanently in the system to comprise a patient case library.

Figure 6:
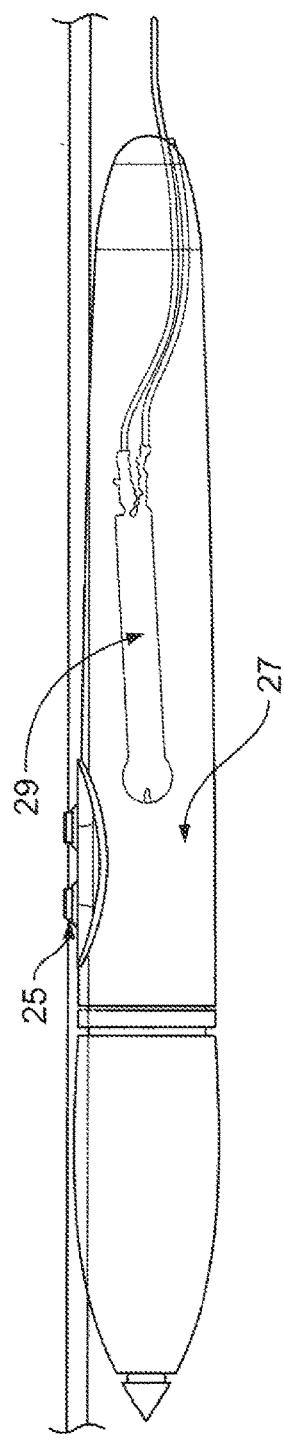
FIG. 6 illustrates one example of a haptic stylus that can be used in a haptic augmented and virtual reality system of the present technology.

A user can begin the performance of simulated cerebral aneurysm clipping by first being seated at the open surgery station 10, and becoming familiar with the input and interaction devices, including haptic stylus 27, which can have a least one input device, such as ON/OFF toggle button 25, or a pinch attachment 29, as shown in FIG. 6. Pinch attachment 29 can measure the angle between the user's thumb and index fingers to simulate both discrete or gradual opening and closing of a virtual surgical instrument. Another example of an input device for a haptic stylus 27 would be a scissors-grip attachment.

1. Selection of a Patient Case and Preparation of the Head for Surgery

Figure 14:
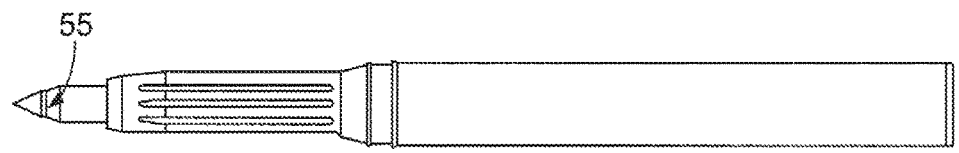
FIG. 14 illustrates one example of a virtual surgical marker that can be provided in an instrument library in a haptic augmented and virtual reality system of the present technology.
Figure 15:
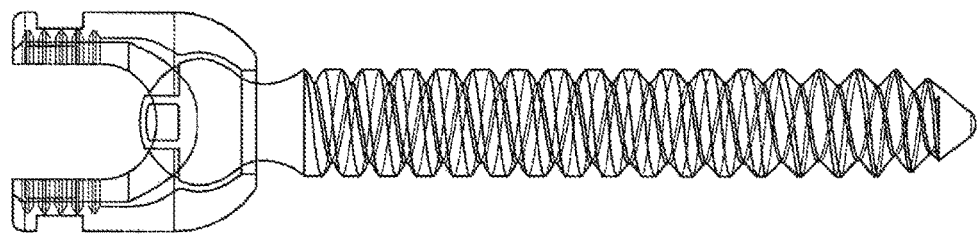
FIG. 15 illustrates one example of a virtual screw that can be provided in an instrument library in a haptic augmented and virtual reality system of the present technology.
Figure 16A:
FIG. 16A illustrates one example of a virtual_acorn drill bit that can be provided in an instrument library in a haptic augmented and virtual reality system of the present technology.
Figure 16B:
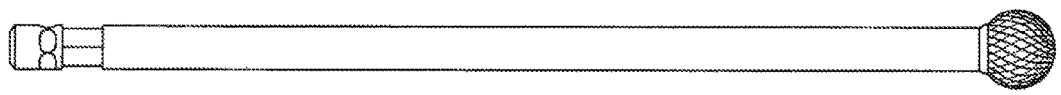

Using the graphics user interface (GUI) 43, which can be displayed on screen 28 and reflected on partially transparent mirror 30 or displayed on an auxiliary tablet computer, the user can select a particular case from the patient case library 140. The user can be visually presented with a virtual patient head, which the user can grasp and rotate into proper position by using a haptic stylus 27. From instrument library 120 the user can perform the select instrument task 121, and thus select a surgical marker 55 (FIG. 14). The system logic can automatically superimpose an image of the surgical marker over the real haptic stylus 27 visible through partially transparent mirror 30. Using this virtual marker 55 the user can draw an outline of the intended craniotomy on the skin of the virtual patient head. One example of possible craniotomy location is a pterional (frontotemporal) craniotomy. The user can inform the system of completion of the craniotomy marking task through a system input device (e.g., GUI, foot pedal, auxiliary tablet computer, etc.). The system can then simulate the appearance of the head by automatically removing the skin in the intended craniotomy region.

2. Burr Bole Drilling (Task 84).

Figure 11:
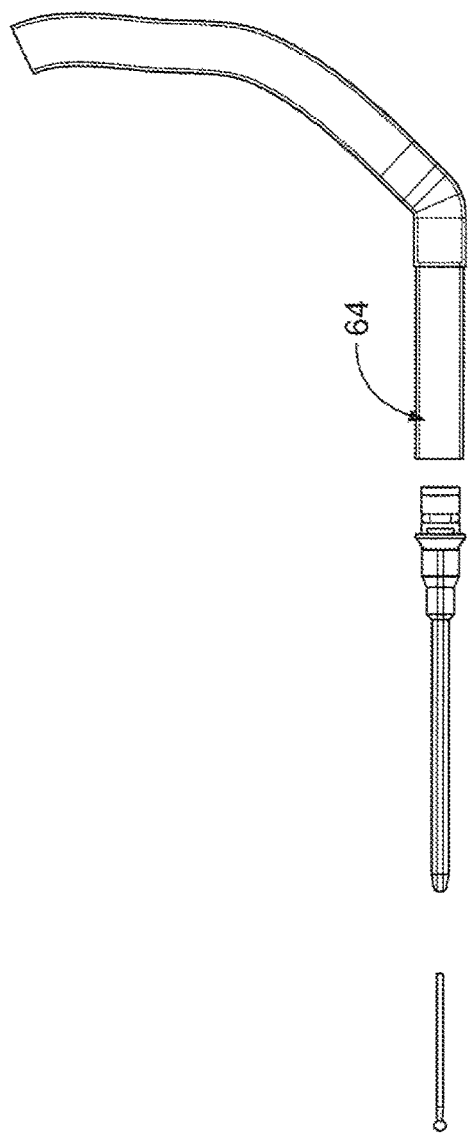
FIG. 11 illustrates one example of a virtual burr tool 64 that can be provided in an instrument library in a haptic augmented and virtual reality system of the present technology.

The user can select a burr tool 64 (FIG. 11) from instrument library 120. The system can superimpose an image of the tool over the real haptic stylus 27 visible through partially transparent mirror 30. The user handle the virtual burr tool 64 by manipulating a haptic stylus 27, and can turn on the virtual burr tool by activating an input device such as a foot pedal 34 or the haptic stylus input device 25. The user can proceed to user task make burr holes 84, and can drill a plurality of burr holes through the simulated cranium, avoiding penetration of the simulated dura mater. Simultaneously in real time, the system logic can perform system task 110 and continuously update the skull geometry using skull 3D volume 131. The system's volume haptics rendering module 112 calculates the force that the user is exerting on the tool to progressively remove the bone volume and outputs the force result to the haptic stylus 27. The system's volume graphics rendering module 113 calculates the progressive visual disappearance of bone volume and outputs the result to the stereoscopic display 28. The user can inform the system of task completion, and in some examples, the system can calculate and record a score for the task, which can be displayed at any time.

3. Craniotomy (Task 85).

Figure 9:
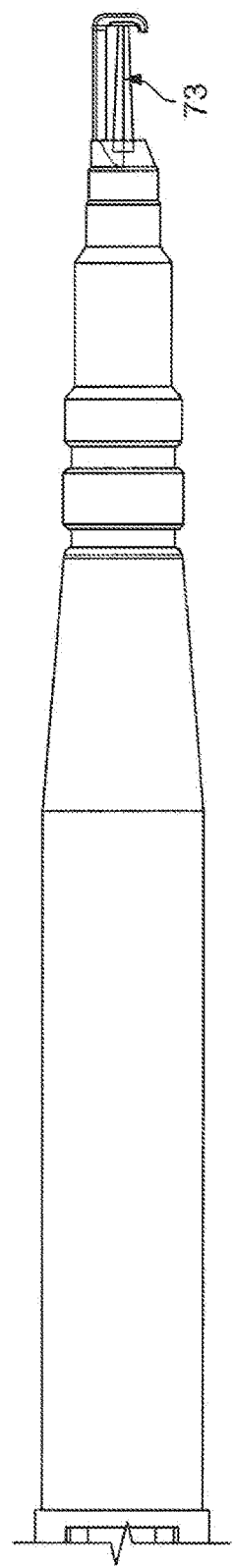
FIG. 9 illustrates one example of a virtual craniotome that can be provided in an instrument library in a haptic augmented and virtual reality system of the present technology.
Figure 17:
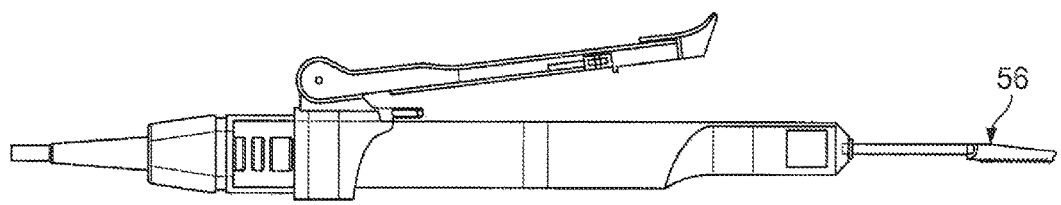
FIG. 17 illustrates one example of a virtual reciprocating saw that can be provided in an instrument library in a haptic augmented and virtual reality system of the present technology.

The user can select a virtual craniotome 73, as illustrated in FIG. 9, from instrument library 120. The system logic superimposes an image of the virtual craniotome 73 over the real haptic stylus 27. The user handles the virtual craniotome 73, at user task 65, by manipulating a haptic stylus 27, and can turn on the virtual craniotome 73 by activating an input device such as a foot pedal 34 or the haptic stylus input device 25. The user can proceed to connect the previously drilled burr holes by performing a craniotomy at user task 85, which can include cutting the cranial bone volume between the holes so as to create a craniotomy bone flap using for example a virtual reciprocating saw 56 (FIG. 17). Simultaneously in real time, the system logic progressively updates the skull geometry at system task 110 using the skull 3D volume 131. The volume haptics rendering module 112 calculates the force that the user is exerting on the tool to progressively remove the bone volume and outputs the force result to the haptic stylus 27. The volume graphics rendering module 113 calculates the progressive visual disappearance of bone volume and outputs the result to the display 28. The user can inform the system of task completion, and in some examples, the system can calculate and record a score for the task, which can be displayed at any time.

4. Opening of Dura Mater (Task 86).

Figure 18:
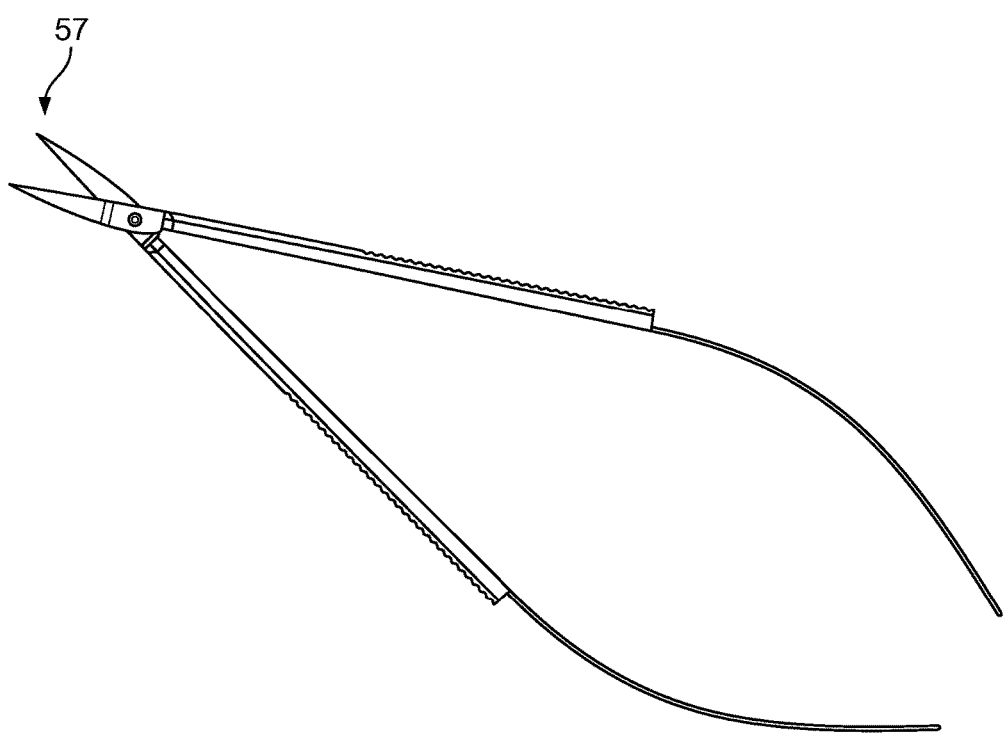
FIG. 18 illustrates one example of a virtual microscissors that can be provided in an instrument library in a haptic augmented and virtual reality system of the present technology.

The user selects microscissors 57, as illustrated in FIG. 18, from instrument library 120. The system logic superimposes an image of the virtual microscissors 57 over the real haptic stylus 27. The user handles the microscissors, user task 66, and can opens and close the virtual microscissors 57 by the haptic stylus input device 25. The user can proceed to cut an opening in the simulated dura mater according to prescribed surgical protocols, user task 86. Simultaneously in real time, the system logic progressively updates the dura mater 3D mesh 132 for the emerging dural opening, system task 111, by using the system's position-based dynamics computation module 116. Based upon position-based dynamics the system's polygonal haptics rendering module 44 calculates the force that the user is exerting on the tool to progressively cut the dura and outputs the force result to the haptic stylus 27. The system's polygonal graphics rendering module 46 calculates the progressive visualized cutting of the dura and outputs the result to the display 28. The user can inform the system of task completion, and in some examples, the system can calculate and record a score for the task, which can be displayed at any time.

At the completion of the dural opening, display of the virtual patient head with craniotomy and dural opening can be transferred from the open surgery station 10 to the microsurgery station 11. In examples where different computers are used for the open surgery station 10 and the microsurgery station 11, data for the virtual patient head can be transferred from the computer at the open surgery station 10 to the computer at the microsurgery station 11. This transfer may be set to occur automatically upon signaled completion of the dural opening, or it may be separately requested by the user. The user can also physically move from the open surgery station 10 to the microsurgery station 11.

5. Sylvian Fissure Dissection with Artificial Blood Flow Modeling Outside the Vessels (Task 83).

The Sylvian fissure (lateral sulcus), which divides the brain's frontal lobe from the temporal lobe, is the major anatomical structure that must be opened to access many aneurysms of the anterior circulation, for example on the middle cerebral artery. The fissure can be accessed by a pterional (frontotemporal) craniotomy, as described above, but the description here and the claims below apply to any placement of craniotomy (e.g., retrosigmoid) and any open surgical access method to reach a cerebral aneurysm.

Figure 10:
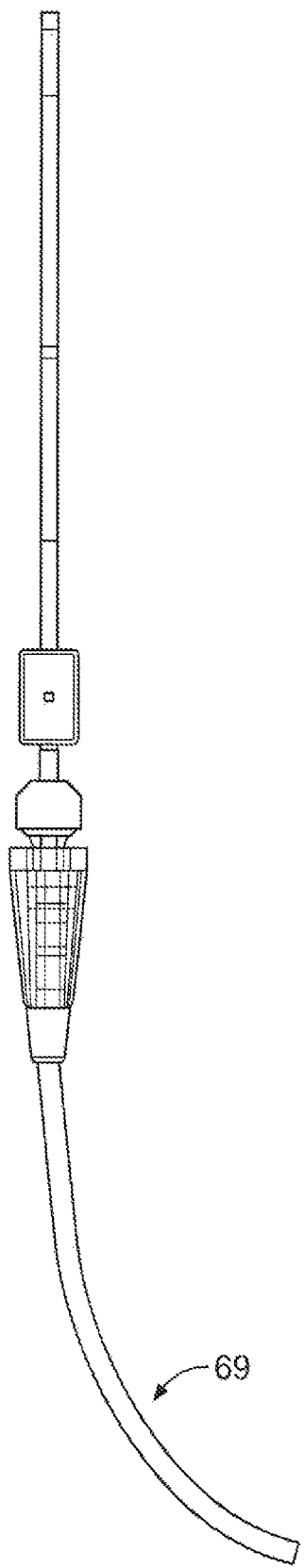
FIG. 10 illustrates one example of a virtual suction tip 69 that can be provided in an instrument library in a haptic augmented and virtual reality system of the present technology.
Figure 12:
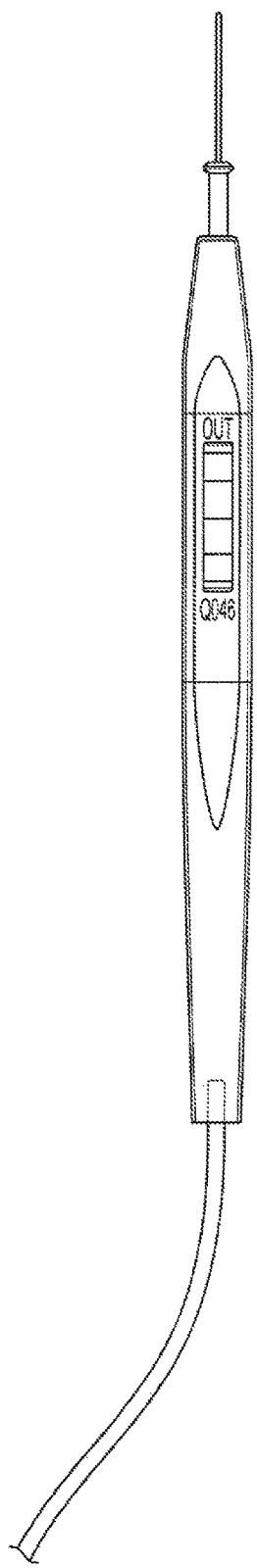
FIG. 12 illustrates one example of a virtual cauterizer that can be provided in an instrument library in a haptic augmented and virtual reality system of the present technology.
Figure 13:
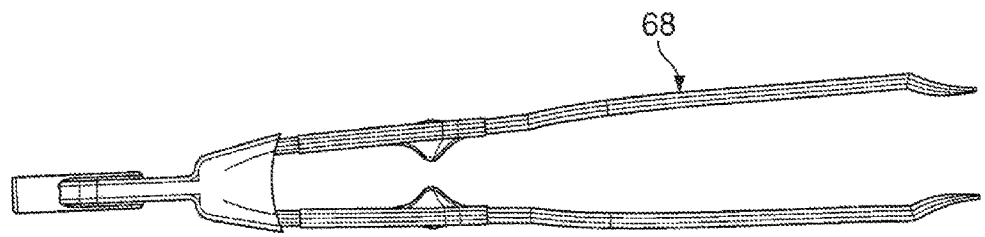
FIG. 13 illustrates one example of a virtual bipolar electrocautery forceps that can be provided in an instrument library in a haptic augmented and virtual reality system of the present technology.

To begin a virtual Sylvian fissure dissection, user task 83, the user can be seated at the microsurgery station 11, which can include a binocular surgical eyepiece 31, foot pedals 34, and two haptic devices for bimanual surgical technique, with each device having a haptic stylus 27, as shown in FIG. 4. The user will typically select two or more virtual surgical tools from instrument library 120. These may include, for example, for the left hand a virtual suction tip 69, illustrated in FIG. 10, and for the right or dominant hand a virtual dissection tool such as an virtual arachnoid knife 70, micro scissors 57, illustrated in FIG. 18, or bipolar electrocautery forceps 68, illustrated in FIG. 13, cauterizer (FIG. 12) with a possibility of changing instruments at any time. The system logic superimposes an image of the virtual suction tip 69 (FIG. 10) and of the virtual dissection tool over the left-hand and right-hand haptic styluses, respectively. The action of the instruments may be activated by a foot pedal 34 or by a haptic stylus input device 25. With the right or dominant hand the user handles the virtual dissection tool such as the bipolar forceps, user task 68, and cuts the tissues within the Sylvian fissure (for example) that adhere to and connect the frontal and temporal lobes, so as to open the Sylvian fissure, user task 83. With the left hand the user handles the suction tip, user task 69, and activates the suction so as to absorb any simulated blood flow in the fissure outside the blood vessels, user task 123, which originates from the dissection of the virtual fissure tissues and is not already coagulated by the virtual bipolar forceps. Simultaneously in real time, the system's artificial (not physics-based) blood flow rendering module 137 progressively updates the appearance and amount of simulated blood flow outside the vessels and its absorption by the suction tool, system task 123, and outputs the result to the display 28. Furthermore, the system logic progressively updates the brain 3D mesh 133 so as to deform the brain for the emerging Sylvian fissure opening, system task 114, by using the system's position-based dynamics computation module 116. Based upon position-based dynamics the system's polygonal haptics rendering module 44 calculates the force that the user is exerting on the dissection tool to cut the tissues that connect the frontal lobe and temporal lobes and outputs the force result to the haptic stylus 27. The system's polygonal graphics rendering module 46 calculates the progressive visualized cutting of the tissues in the Sylvian fissure and outputs the result to the display 28. The dissection task for the Sylvian fissure is considered complete when the aneurysm of interest becomes visible and accessible at the bottom of the fissure. The user can inform the system of task completion, and in some examples, the system can calculate and record a score for the task, which can be displayed at any time.

6. Brain Retraction (Task 87).

In past medical practice mechanical brain retraction was often performed in the early phases of opening the Sylvian fissure, and this can also be simulated by the haptic and virtual reality system using the haptic and virtual reality station 10 as described here. However, several current medical guidelines recommend creation of a wide opening of the Sylvian fissure by drainage of cerebrospinal fluid and dissection of tissues, without mechanical brain retraction. After the fissure has been opened, a malleable metal brain spatula can be applied to hold (not to retract) one of the lobes of the brain, such as the frontal or temporal lobe, to provide a better view of the aneurysm. The user selects a retractor in the form of a virtual brain spatula 67 from instrument library 120. The system logic superimposes an image of the tool over the real haptic stylus 27. The user handles the virtual brain retractor, user task 67, and proceeds to place the retractor against one of the exposed lobes of the virtual brain so as to hold the dissected surgical line of access open for the dissection of tissues around the aneurysm and clipping of the aneurysm. Simultaneously in real time, the system logic progressively updates the brain 3D mesh 133 for the retracted brain, system task 114, by using the system's position-based dynamics computation module 116. Based upon position-based dynamics the system's polygonal haptics rendering module 44 calculates the force that the user is exerting on the retractor to hold the brain in position, and outputs the force result to the haptic stylus 27. The system's polygonal graphics rendering module 46 calculates the progressive visualized movement or deformation of the brain and outputs the result to the display 28. The user informs the system of task completion and receives a score.

7. Sylvian Fissure Dissection with Artificial Blood Flow Modeling Outside the Vessels (Task 83).

The Sylvian fissure (lateral sulcus), which divides the brain's frontal lobe from the temporal lobe, is the major anatomical structure that must be opened to access many aneurysms of the anterior circulation, for example on the middle cerebral artery. The fissure can be accessed by a pterional (frontotemporal) craniotomy, as described above, but the description here and the claims below apply to any placement of craniotomy (e.g. retrosigmoid) and any open surgical access method to reach a cerebral aneurysm.

8. Dissection Around Aneurysm (Task 89).

The Sylvian fissure dissection task 83 concludes when a sufficiently wide opening and pathway to the parent vessel and aneurysm has been created. The next surgical step is to dissect carefully around the aneurysm parent vessel, neck, and dome or sac, without unnecessarily sacrificing nearby micro-vessels, so as to prepare an open space in which an aneurysm clip can be placed without inadvertently clipping other vessels and without unduly narrowing the parent vessel. In live surgery this task is continuous with the Sylvian fissure dissection, and the surgeon uses the same tools, typically a suction tip, user task 69, and a knife, microscissors, or bipolar forceps, user task 68. Similarly, the system functions are the same as in the Sylvian fissure dissection. The system logic progressively updates the brain 3D mesh 133 to show the deformation of vessels, system task 115, that results from the dissection around the aneurysm. Based upon position-based dynamics the system's polygonal haptics rendering module 44 calculates the force that the user is exerting on the dissection tool to cut or manipulate the tissues and blood vessels, and outputs the force result to the haptic stylus 27. The system's polygonal graphics rendering module 46 calculates the progressive visualized dissection around the aneurysm and outputs the result to the display 28.

9. Choosing of an Aneurysm Clip and Closing of Clip on Aneurysm Neck (Tasks 90 and 91).

Figure 7:
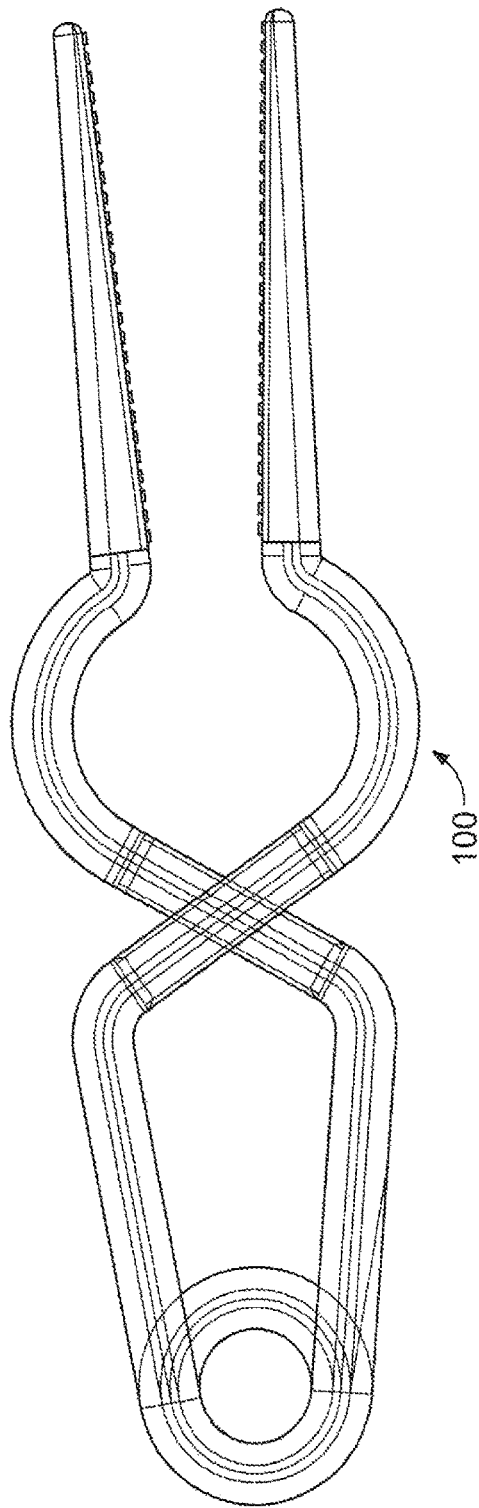
FIG. 7 illustrates one example of a virtual aneurysm clip that can be provided in an instrument library in a haptic augmented and virtual reality system of the present technology.
Figure 8:
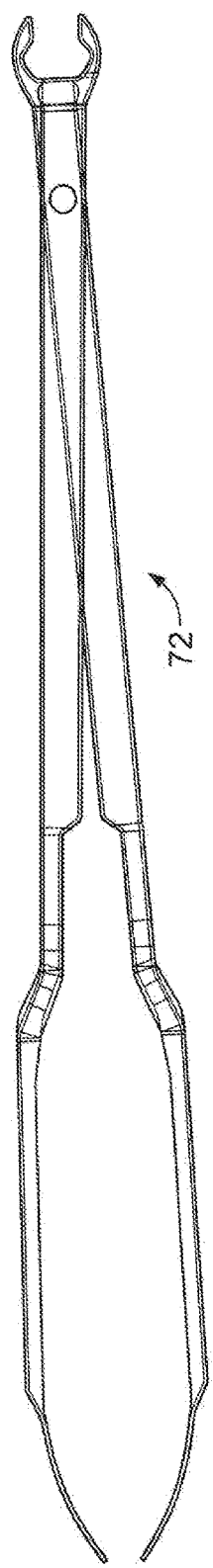
FIG. 8 illustrates one example of a virtual aneurysm clip holder that can be provided in an instrument library in a haptic augmented and virtual reality system of the present technology.

Aneurysm clip selection is a crucial part of the operation because there are many different shapes, sizes, and positions of aneurysms and a corresponding wide variety of clips of different sizes, shapes (straight, curved), and designs (e.g., fenestrated clips that go around one vessel to clip another). Based on a direct line of sight of the virtual aneurysm on the simulator as well as on patient-specific cerebral angiograms stored in the patient case library 140, the user performs the aneurysm clip selection, user task 90, to select an appropriate virtual aneurysm clip 100 from clip library 71. The system logic superimposes an image of an aneurysm clip holder 72 (see FIG. 72) together with clip 100 (see FIG. 7) over the real haptic stylus 27. The user handles the clip holder, user task 72, and applies differential finger pressure to a haptic stylus input device such as ON/OFF toggle button 25, or a pinch attachment 29 (FIG. 6) to hold the clip or to close and release the clip. After taking an initial measurement of blood flow in the parent artery by means of a virtual perivasular flow sensor (see below), the user proceeds to place the clip snugly around the virtual aneurysm neck and to close it on the neck so as to seal off the pulsatile blood flow from the parent artery into the aneurysm sac, thus rendering the aneurysm clinically harmless. Simultaneously in real time, the system logic progressively updates the brain 3D mesh 133 to show the deformation of vessels, system task 115, that results from placing the clip around the aneurysm neck. Based upon position-based dynamics the system's polygonal haptics rendering module 44 calculates the force that the user is exerting on the virtual clip holder 72 (FIG. 8) to deform the blood vessel and aneurysm, and outputs the force result to the haptic stylus 27. The system's polygonal graphics rendering module 46 calculates the progressive visualized closing of the clip around the aneurysm and outputs the result to the display 28. The user informs the system of task completion, and the score for the aneurysm clipping is determined by the next step, testing of the parent artery blood flow.

10. Flow Testing of Parent Artery Before and after Aneurysm Clip Placement (Task 92).

Success in aneurysm clipping is achieved by (a) fully clipping the aneurysm neck so that there is no remaining pulsatile blood flow through the neck into the aneurysm sac; (b) avoiding entrapment of other nearby small perforating arteries within the grasp of the clip; and (c) avoiding clip placement too close to the parent artery, which would reduce its inner diameter and therefore its blood flow. While the success of the first two tasks is determined visually, success of the third task, preserving blood flow in the parent artery, is determined by testing the flow in the parent artery before and after clip placement. A standard real-life method is to use an ultrasonic perivascular flow sensor, placed around the parent artery, that relies on the principle of transit-time ultrasound volume flow measurement and outputs blood flow in units of mL/min, but other methods of quantitative flow measurement are included. The present haptic augmented and virtual reality system simulates the change of parent artery blood flow after placement of a virtual aneurysm clip, together with the measurement of this change by a virtual flow probe, on the basis of the clip's final position and a precalculated table of vessel diameters, blood pressures, and flow values, system task 144, rather than by a fully realistic computational fluid dynamics simulation of the blood flow and of the operation of the virtual ultrasonic probe.

To make a quantitative volumetric measurement of the virtual blood flow in the parent artery before and after aneurysm clipping, the user selects the ultrasonic perivascular flow sensor 75 from instrument library 120. The system logic superimposes an image of the virtual flow sensor over the real haptic stylus 27. The user handles the flow sensor, user task 75, and proceeds to place the C-shaped head of the sensor around one or more sections of the proximal parent artery and/or its distal branches. Simultaneously in real time, the system logic progressively updates the brain 3D mesh 133, which includes the vessels and the aneurysm, to reflect the pressure of the sensor on the parent artery and the artery's consequent deformation, system task 115, by using the system's position-based dynamics computation module 116. Based upon position-based dynamics the system's polygonal haptics rendering module 44 calculates the force that the user is exerting on the sensor while measuring the blood flow and outputs the force result to the haptic stylus 27. The system's polygonal graphics rendering module 46 calculates the progressive visualized deformation of the parent artery and outputs the result to the display 28. The user performs the flow measurement on the parent artery before and after clipping its aneurysm. The system calculates these two volumetric flow values in mL/min, system task 144, and outputs these values as well as the difference to display 28. The user either accepts the result if the parent artery blood flow is not reduced beyond a predetermined percentage of its pre-clipping value (e.g., 25 percent maximum reduction), in which case the simulation exercise is completed and the user receives an aneurysm clipping score and a comprehensive score. Otherwise, the user can reposition the clip and retest the blood flow, or can select a new clip, task 90, from library 71 and repeat the exercise.

As an additional means of virtual blood flow testing, the system can simulate the intraarterial injection of an indocyanine green (ICG) contrast agent used for diagnostic fluorescence angiography, wherein the flow of the contrast agent inside the vessels is visualized by a virtual gamma camera. The simulator user requests the injection of the ICG through the system's graphic user interface, which counts as the user's performance of task 92, flow testing of parent artery after clip placement. The system then performs task 117, render the blood flow by means of smooth particle hydrodynamics, which is a real-time (interactive) physics-based approximation method, but not a fully accurate (and time consuming) computational fluid dynamic simulation. The visualized contrast injection of task 117 is output to the graphic display 28. The virtual ICG injection visualizes the blood flow in distal branches the parent artery downstream from the aneurysm neck and clip, but it can also visualize blood flow in smaller perforating arteries near the parent artery to ensure that they have not been accidentally included in the grasp of the virtual aneurysm clip. Perforating arteries below the resolution of current medical imaging devices (cf. input source 44) can be modeled manually and added to the blood vessel 3D mesh 134.

11. Optional Aneurysm Rupture Simulation (Task 74).

An aneurysm may rupture at any time but particularly during the dissection around the aneurysm, user task 89, or the placing of the aneurysm clip, user task 91. The system can be programmed to simulate an aneurysm rupture as a random event to test user emergency response, or to simulate a rupture in response to a user surgical error. When a rupture is simulated, system task 74, the system deforms the aneurysm sac, system task 115, then uses position-based dynamics, system task 116, and polygonal graphics rendering, system task 46, to output the visual result to display 28. When an aneurysm ruptures, the system also renders artificial blood flow into the subarachnoid space, system task 137, and outputs the visual result to display 28

The simulation method can include evaluation of a user's performance. A user can be scored based on patient head positioning, craniotomy positioning and cutting, dural opening, aneurysm clip selection, left-handed and right-handed clip manipulation, repositioning of misplaced clips, use of suction tip and bipolar electrocautery, total attempts at clip placement, and responses to errors, including aneurysm rupture, incomplete clipping, clips too distant from parent vessel, unacceptable narrowing of parent vessel as determined by flow testing, etc. The simulator can record a score on each of the surgical steps or error recovery strategies, with appropriate weighting to yield an overall comprehensive score.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A haptic augmented and virtual reality system for performing simulated surgical procedures that include open surgery steps and microsurgery steps, the system comprising:

A) an open surgery station comprising:
 a first haptic device comprising a hand-held stylus and driven by haptics rendering logic, wherein the first haptic device tracks a user's hand movements and provides force feedback to the user;
 a first display system driven by graphics logic, wherein the first display system comprises a display screen and a head tracking system, and provides a dynamic user-centered perspective of open surgical views of a portion of a virtual patient's anatomy and at least a first virtual surgical instrument, wherein the virtual instrument is visually superimposed over the hand-held stylus of the haptic device, permitting the user to see both the virtual instrument and the user's hands, and moves as the stylus moves based on data received from the first haptic device; and
 open surgery station logic that integrates the haptics rendering logic and the graphics logic and provides real-time simulation of the open surgery steps of the surgical procedure, including updating the open surgical views in real time in response to user operations performed with the first haptic device and according to the position and orientation of the user's head given by the head tracking system; and B) a microsurgery station comprising:
 a second haptic device driven by haptics rendering logic, wherein the second haptic device tracks the user's hand movements and provides force feedback to the user;
 a second display system driven by graphics logic, wherein the second display system comprises a binocular surgical microscope eyepiece and display screens configured to allow the user to acquire depth perception, and provides microsurgical views of a portion of the virtual patient's anatomy and at least a second virtual surgical instrument whose position is simulated based on data received from the second haptic device; and
 microsurgery station logic that integrates the haptics rendering logic and the graphics logic and provides real-time simulation of the microsurgery steps of the surgical procedure including updating the microsurgical surgical views in real time in response to user operations performed with the second haptic device.

2. The system of claim 1, wherein the first haptic device comprises a pinch attachment that measures the angle between a user's thumb and index fingers to simulate both discrete or gradual opening and closing of a virtual surgical instrument.

3. The system of claim 1, wherein the open surgery station logic comprises an instrument library that includes a plurality of virtual surgical instruments that can each be selected by a user and displayed by the first display system.

4. The system of claim 3, wherein the virtual surgical instruments include a burr tool, a craniotome, and micro-scissors.

5. The system of claim 1, wherein the microsurgery station logic comprises an instrument library that includes a plurality of virtual surgical instruments that can each be selected by a user and displayed by the first display system.

6. The system of claim 5, wherein the virtual surgical instruments include bipolar forceps, an arachnoid knife, a brain retractor, a suction tip, a clip holder, an ultrasound blood flow probe, a dissection tool, and micro-scissors.

7. The system of claim 5, wherein the microsurgery station further comprises at least one foot pedal that activates at least one of the virtual surgical instruments that can be selected from the second instrument library.

8. The system of claim 1, wherein the binocular surgical microscope eyepiece is movable with respect to the display system.

9. The system of claim 1, wherein the binocular surgical microscope eyepiece is mounted on a height adjustable mounting frame.

* * * * *